US008362903B2

(12) United States Patent
Lindh et al.

(10) Patent No.: US 8,362,903 B2
(45) Date of Patent: Jan. 29, 2013

(54) SYSTEM AND METHOD FOR PROVIDING ENHANCED WEIGHT ALERT NOTIFICATION DURING AUTOMATED PATIENT MANAGEMENT

(75) Inventors: Par Lindh, Maple Grove, MN (US); Donovan Benton Fellows, Woodbury, MN (US); Timothy E. Meyer, North Oaks, MN (US); Paul Jones, St. Paul, MN (US); Kenneth I. Tobacman, Cedar, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 944 days.

(21) Appl. No.: 12/432,939

(22) Filed: Apr. 30, 2009

(65) Prior Publication Data

US 2009/0278696 A1   Nov. 12, 2009

Related U.S. Application Data

(60) Provisional application No. 61/051,260, filed on May 7, 2008.

(51) Int. Cl.
*G08B 23/00* (2006.01)

(52) U.S. Cl. ............. 340/573.1; 340/539.1; 340/539.11; 340/539.13; 340/665; 340/666; 340/667

(58) Field of Classification Search ............... 340/573.1, 340/665, 666, 667, 539.1, 539.11, 539.13
See application file for complete search history.

(56) References Cited

U.S. PATENT DOCUMENTS

| 6,336,903 | B1 | 1/2002 | Bardy |
| 6,368,284 | B1 | 4/2002 | Bardy |
| 6,398,728 | B1 | 6/2002 | Bardy |
| 6,411,840 | B1 | 6/2002 | Bardy |
| 6,440,066 | B1 | 8/2002 | Bardy |
| 2006/0116557 | A1* | 6/2006 | Moore et al. ................. 600/300 |
| 2006/0253300 | A1 | 11/2006 | Somberg et al. |
| 2006/0253301 | A1 | 11/2006 | Simms et al. |
| 2007/0180047 | A1 | 8/2007 | Dong et al. |
| 2010/0063840 | A1 | 3/2010 | Hoyme et al. |

* cited by examiner

*Primary Examiner* — Daryl Pope
(74) *Attorney, Agent, or Firm* — Pauly, Devries Smith & Deffner, L.L.C.

(57) ABSTRACT

A system and method for providing enhanced weight alert notification during automated patient management is presented. A plurality of weight measurements in an automated patient environment from a weight monitoring device for a patient during an observation period is remotely obtained. A raw baseline weight for the patient is determined based on a function of the weight measurements. Irregularities in the weight measurements are identified. The raw baseline weight is processed into a baseline weight by application of a correction coefficient to the irregularities. Weight remotely measured in the automated patient environment for the patient on a substantially regular basis is obtained. Changes in the weight are identified by periodic comparison to the baseline weight. An alert notification is generated in response to the change in weight.

23 Claims, 7 Drawing Sheets

SYSTEM AND METHOD FOR PROVIDING ENHANCED WEIGHT ALERT NOTIFICATION DURING AUTOMATED PATIENT MANAGEMENT

This application claims the benefit of U.S. Provisional Application No. 61/051,260, filed May 7, 2008, the content of which is herein incorporated by reference in its entirety.

FIELD

The invention relates in general to automated patient management and, specifically, to a system and method for providing enhanced weight alert notification during automated patient management.

BACKGROUND

Weight change can have significance in disease diagnosis and management. For example, edema is an abnormal increase of fluids in the organs of a patient, which can present as sudden weight gain. More particularly, pulmonary edema is one indication of impending heart failure and a sudden, unexplained weight gain could signify disease onset. Conversely, other weight changes may not hold clinical significance. For instance, many women of child-bearing age experience temporary weight gain due to bloating during their menstrual cycle. Other weight changes may simply be improperly realized. For example, clinics may vary in how they measure patient weight and differences in observed weight may be attributed to procedural and not clinical explanation.

Weight change can be followed through automated patient management, which enables a clinician, such as a physician, nurse, or other healthcare provider, to monitor patient well-being through homecare medical devices that can collect and forward patient physiometry without requiring the presence or assistance of medical personnel. Advances in automation have encouraged such self-care solutions and public data communications networks, in particular, the Internet, have made ready data retrieval and patient communication viable and widely available. Utilizing a weight monitoring device within an automated patient management environment facilitates regular monitoring and analysis of patient weight.

SUMMARY

A system and method includes remotely monitoring a patient in an automated patient management environment for potentially actionable changes in the weight of the patient. Weight measurements are obtained for the patient over a specified period of time through a weight monitoring device, such as a scale. The weight measurements are analyzed over time to produce a baseline weight for the patient. The baseline weight can be determined as a function of a cumulative or statistical analysis of the weight measurements. The weight measurements can be adjusted using a correction coefficient based on various extrinsic conditions. After applying the correction coefficient, a particular weight measurement can be used "as is," adjusted to some degree, or completely discarded. Thereafter, the patient's weight is regularly monitored for changes in weight and compared to the baseline weight. A weight gain or loss outside of a prescribed norm can trigger an action, such as tiered alert notification.

One embodiment provides a system and method for performing actions in response to enhanced weight monitoring during automated patient management. A plurality of weight measurements remotely measured in an automated patient environment for a patient during an observation period is obtained. A raw baseline weight for the patient is determined based on the weight measurements. The raw baseline weight is adjusted through processing of irregularities in the weight measurements into a baseline weight. Weight remotely measured in the automated patient environment for the patient on a substantially regular basis is obtained. Changes in the weight are identified by periodic comparison to the baseline weight. Action is taken in response to the periodic comparison upon at least one of the changes exceeding a prescribed extent of change over the baseline weight.

A further embodiment provides a system and method for providing enhanced weight alert notification during automated patient management. A plurality of weight measurements is remotely obtained in an automated patient environment from a weight monitoring device for a patient during an observation period. A raw baseline weight for the patient is determined based on a function of the weight measurements. Irregularities in the weight measurements are identified. The raw baseline weight is processed into a baseline weight by application of a correction coefficient to the irregularities. Weight remotely measured in the automated patient environment for the patient on a substantially regular basis is obtained. Changes in the weight are identified by periodic comparison to the baseline weight. An alert notification is generated in response to the change in weight.

Still other embodiments will become readily apparent to those skilled in the art from the following detailed description, wherein are described embodiments of the invention by way of illustrating the best mode contemplated for carrying out the invention. As will be realized, other and different embodiments are possible and their several details are capable of modifications in various obvious respects, all without departing from the spirit and the scope. Accordingly, the drawings and detailed description are to be regarded as illustrative in nature and not as restrictive.

While the invention is susceptible to various modifications and alternative forms, specifics thereof have been shown by way of example and drawings, and will be described in detail.

It should be understood, however, that the invention is not limited to the particular embodiments described. On the contrary, the intention is to cover modifications, equivalents, and alternatives falling within the spirit and scope of the invention.

DETAILED DESCRIPTION

Automated Patient Management

Automated patient management encompasses a range of activities, including remote patient management and automatic diagnosis of patient health, such as described in commonly-assigned U.S. Patent Pub. No. US2004/0103001, published May 27, 2004, pending, the disclosure of which is incorporated by reference. Such activities can be performed proximate to a patient, such as in the patient's home or office; centrally through a centralized server, such as from a hospital, clinic or physician's office; or through a remote workstation, such as a secure wireless mobile computing device.

Figure 1:
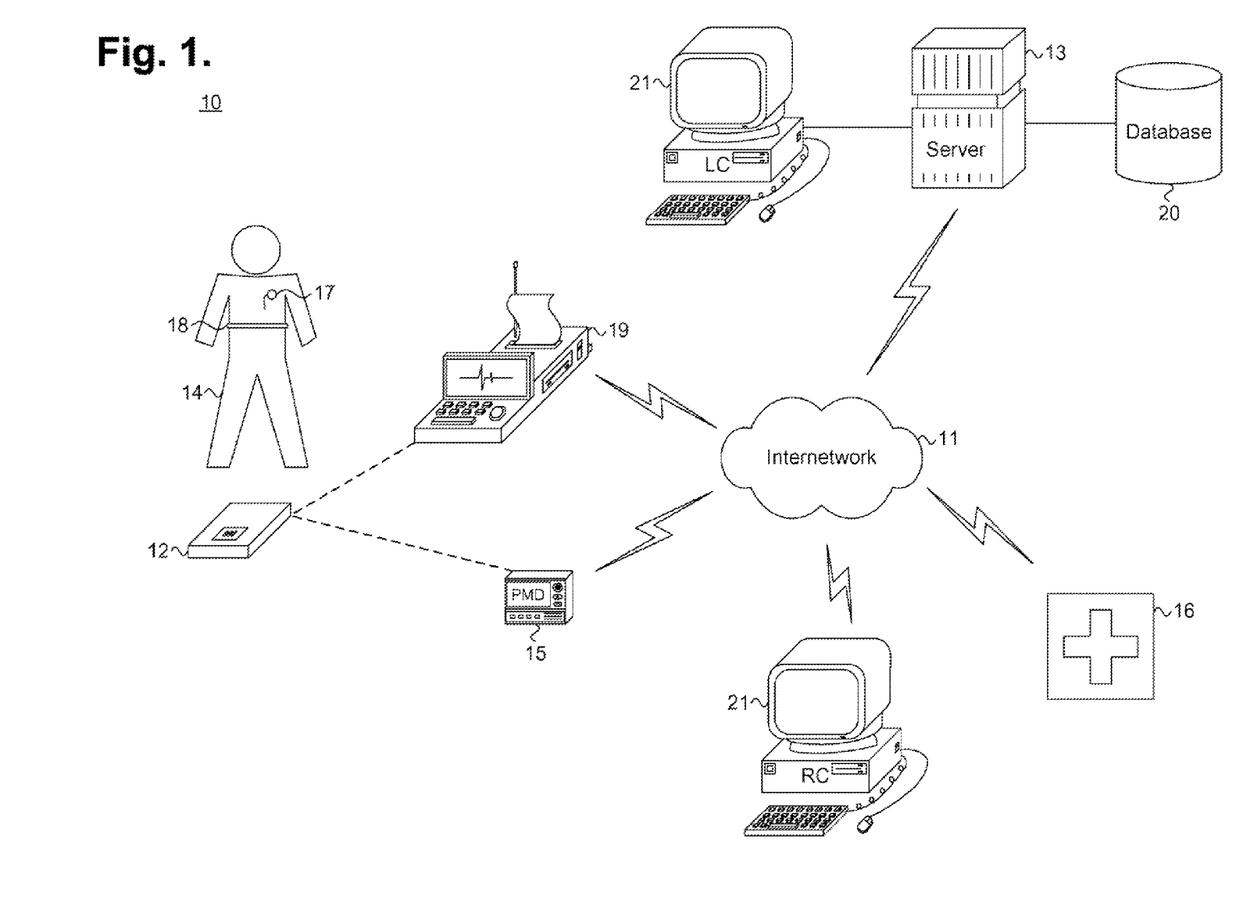
FIG. 1 is a functional block diagram showing, by way of example, an automated patient management environment.

Automated patient management also enables remote monitoring of patient weight, allowing for configuring and triggering of alert notifications when the patient's weight exceeds a prescribed norm or range. FIG. 1 is a functional block diagram showing, by way of example, an automated patient management environment 10. In one embodiment, a patient 14 has a weight monitoring device 12, such as a weight scale that includes a data interface, which is interconnected remotely to a centralized server 13 over an internetwork 11, such as the Internet, or through a public telephone exchange (not shown), such as a conventional or mobile telephone network. The weight monitoring device 12 could also be indirectly interconnected via a patient management device (PMD) 15. The PMD 15 includes a patient-operable repeater, or personal computer, including a secure wireless mobile computing device. The centralized server 13 can also be remotely interfaced to a patient care facility 16, such as a clinic or hospital, to ensure online access to medical response or patient care providers. In addition, the internetwork 11 can provide both conventional wired and wireless interconnectivity. In one embodiment, the internetwork 11 is based on the Transmission Control Protocol/Internet Protocol (TCP/IP) network communication specification, although other types or combination of networking implementations are possible. Similarly, other network topologies and arrangements are possible.

The weight monitoring device 12 measures and records the weight measurements of the patient 14 as patient weight data for eventual upload to the server 13. The patient management device 12 collects and temporarily stores the weight data from the weight monitoring device 12 for periodic upload over the internetwork 11 to the server 13 and for storage in a patient record database 20. The weight data could also be provided on demand, for instance, in response to caregiver directions. Other types of patient data collection, reporting internetworks or periodicity, and storage are possible.

Figure 2:
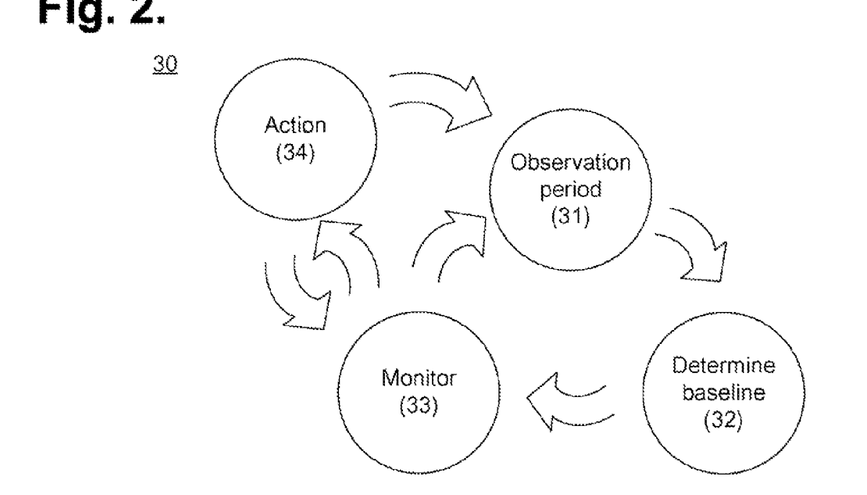
FIG. 2 is a process flow diagram showing a method for providing enhanced weight alert notification during automated patient management, in accordance with one embodiment.

The collected weight data is evaluated by the server 13 and can potentially trigger one or more alert notifications, as further described below beginning with reference to FIG. 2. Alert notification can be performed in the server 13, weight monitoring device 12, PMD 15, or one or more other devices either operating as part of or as an adjunct to the internetwork 11, such as described in commonly-assigned U.S. Patent Pub. No. 2006-0253301, filed May 3, 2005, pending, the disclosure of which is incorporated by reference.

In a further embodiment, the patient 14 is the recipient of an implantable medical device 17, or an external medical device 18, which provides physiometric monitoring or therapy delivery. Patient data is retrieved from the device 17, 18 by the PMD 15 and uploaded to the server 13. In a further embodiment, a programmer 19, including programmer-recorder, can be used in-clinic to interrogate the device 17, 18.

In general, patient data includes physiological measures, which can be quantitative or qualitative; parametric data regarding the status and operational characteristics of the patient data source itself, and environmental parameters, such as the temperature or time of day. Other types of patient data are possible. In a further embodiment, the PMD 15, personal computer, telephone, or facsimile machine also record or communicate qualitative quality of life measures or symptom assessments that reflect the subjective impression of physical well-being perceived by the patient 14 at a particular time.

In a further embodiment, the patient 14 is identified and authenticated prior to collection and upload of the patient weight data through the weight monitoring device 12, or other patient data, such as described in commonly-assigned U.S. Patent Pub. No. US 2007/0180047, published Aug. 2, 2007, pending, the disclosure of which is incorporated by reference. To ensure patient data integrity, the identification of the source of the patient weight data is confirmed against authentication data that uniquely identifies a specific patient 14 prior to being forwarded to the centralized server 13 or other patient data repository. Thus, mistaken identity, inter alia, is avoided.

In a still further embodiment, the collected patient data can be accessed and analyzed by one or more clients 21, either locally-configured or remotely-interconnected over the internetwork 11. The clients 21 can be used, for example, by clinicians to securely access the weight data or other stored patient data assembled in the database 20 and to select and prioritize patients for health care provisioning, such as respectively described in commonly-assigned U.S. patent application Ser. No. 11/121,593, filed May 3, 2005, pending, and U.S. Patent Pub. No. US 2006-0253300, filed May 3, 2005, pending, the disclosures of which are incorporated by reference.

The collected patient data can also be evaluated for the occurrence of one or more conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

In a further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Preferably, the server 13 is a server-grade computing platform configured as a uni-, multi- or distributed processing system, and the clients 21 are general-purpose computing workstations, such as a personal desktop or notebook computer. In addition, the server 13 and clients 21 are programmable computing devices that respectively execute software programs and include components conventionally found in computing device, such as, for example, a central processing unit (CPU), memory, network interface, persistent storage, and various components for interconnecting these components.

Method

Fundamentally, following baseline weight determination, patient weight is taken on a regular basis and weight change outside of a prescribed norm or range may trigger an alert notification, as appropriate. FIG. 2 is a process flow diagram showing a method 30 for providing enhanced weight alert notification during automated patient management, in accordance with one embodiment. The method 30 is performed as a series of process steps by the server 13, or any computing device, in conjunction with the weight monitoring device 12, connected to a network with access to the patient weight data.

The patient's weight is obtained from the weight monitoring device 12 several times throughout an observation period (step 31). Generally, the observation period is over evenly spaced time points, such as consecutive days, and weight is measured preferably at the same time of day. In a further embodiment, the observation period can be over irregular time points. For example, weight measurement can be obtained for representative days of the week, such as Monday, Wednesday, Friday, and Sunday, but not other days, such as Tuesday, Thursday, and Saturday, which may be merely cumulative. Other observation periods are possible.

Once the weight data for the observation period is obtained, a baseline weight for the patient is determined (step 32). The baseline weight can be determined as a function of a cumulative or statistical analysis of the weight data, as further discussed below with reference to FIG. 3. Additionally, the baseline weight can be adjusted, as needed, to counter irregularities observed in the weight measurements during the observation period. Irregularities can include patient particularity, problems with the weight monitoring device 12, or bad weight data values. For example, a correction coefficient based on extrinsic conditions and other factors could be applied to adjust or correct the weight data. Extrinsic conditions that can affect the determination of the baseline weight are evaluated and the weight data can be adjusted accordingly, as further discussed below with reference to FIG. 5. The baseline weight can also be input manually or through automation, as further discussed below with reference to FIG. 3. The baseline weight can be determined based upon the entire observation period or from a subset of the observation period. For example, a statistical baseline weight function can be expressed as:

$$w_{BL}=f(w_i;\{w_1,w_2,w_3,\ldots,w_n\})$$

where $w_{BL}$ is the baseline weight, $f(w_i)$ is a statistical function, and n is the number of individual weight measurements. The statistical function can include mean, average, maximum, minimum, or weighted average of the weight data. Other forms of statistical function are possible.

The weight of the patient is monitored via the weight monitoring device 12 and compared to the baseline weight (step 33). Monitoring is performed preferably over a regular basis, generally per a weigh-in schedule, or as requested or required by a physician. Other monitoring periods are possible. Changes in weight outside a prescribed extent can trigger an action (step 34). For example, an alert notification can be triggered, as further discussed below with reference to FIG. 9. If, during monitoring (step 33) of the patient 14, a new baseline weight is needed, a new observation period (step 31) can begin. A new baseline weight may be needed if the previous baseline weight was inaccurate due to incorrect weight measurements or is no longer valid because of a permanent change in the patient's 14 weight. Other reasons for a new baseline weight are possible. In a further embodiment, monitoring (step 33) can occur during the observation period (step 34). After the action is taken, the patient 14 can continue to be monitored (step 33) or a new observation period (step 31) can commence if a new baseline weight is needed. Alert notifications are active, and can be triggered, during baseline determination.

In a further embodiment, a weight threshold for a specific weight change within a specified period of time can be set. Sudden, short-term weight gain or loss can have clinical significance independent from a baseline weight but may go undetected if the weight gain or loss is within the prescribed extent of weight change. The threshold can be set independently of a baseline weight. The threshold can be a gain or loss in weight of the patient. The gain or loss thresholds can be used in combination or individually. The threshold can be a weight change in weight units, such as pounds or kilograms, or a percentage of the current weight of the patient. The weight of the patient is regularly monitored and once a threshold is crossed, an action can be taken, such as generating an alert notification, as discussed above.

Baseline Determination Parameters

Figure 3:
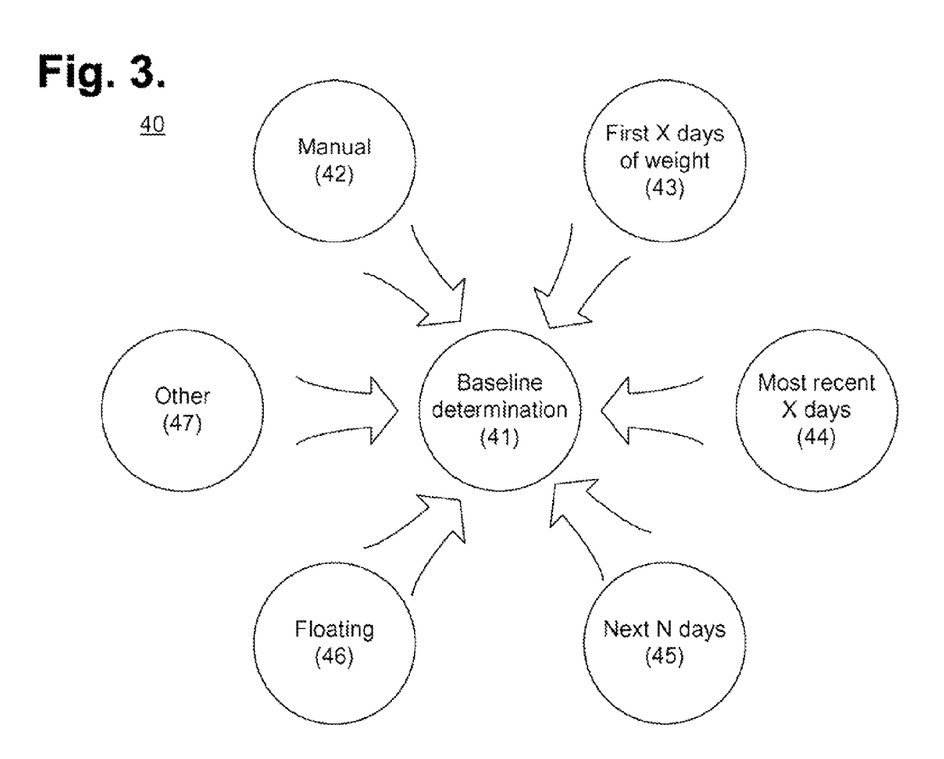
FIG. 3 is a data flow diagram showing, by way of example, baseline weight generation parameters.

Not all weight change is actionable. Weight changes are compared against a baseline weight to determine whether a weight change requiring action has occurred. FIG. 3 is a data flow diagram 40 showing, by way of example, parameters for baseline determination 41 for use in the method of FIG. 2. The parameters for baseline determination 41 can include manual input 42, first number of days of weight 43, most recent number of days of weight 44, next number of days of weight 45, and floating weight 46. A baseline weight can be input manually 42 by the patient, physician, or other healthcare provider. The baseline determination can be automated by conducting a mathematical or statistical analysis of the observed weight data over a period of time, such as a mean, average, minimum, maximum, or weighted average. A weighted average gives more, or less, weight to certain weight data as compared to other weight data. For example, first number of days of weight 43 determines a baseline based on the average of a set number of days occurring on and after a first weight data reading of the patient 14. Additionally, the baseline weight can be set or reset using the average of the weight data from the most recent set number of days 44 of readings. Further, weight data from a set number of future days 45 can be used to set, or reset, a baseline weight. Finally, a floating 46 baseline weight can be determined. The floating 46 baseline weight is recalculated based on a sliding window of a set number of readings from days before the current reading. Other 47 baseline determinations 41 are possible.

During baseline determination, weight data is checked for validity. If a weight data measurement is outside an error range, the weight data measurement is discarded and not used as part of the baseline determination. For example, a weight data measurement can be discarded if the weight data measurement is more than two standard deviations from other weight data measurements. In a further embodiment, the discarded weight data measurement can be used for generating an alert if the weight data measurement meets the alert criteria, as discussed further below with reference to FIG. 4. If a weight data measurement varies sufficiently, the measurement is discarded for both baseline determination and alert notification, as discussed further below with reference to FIG. 4. For example, weight data measurements for consecutive days that vary by more than twenty can be discarded for baseline determination and alert notification.

Alert Notification

Figure 4:
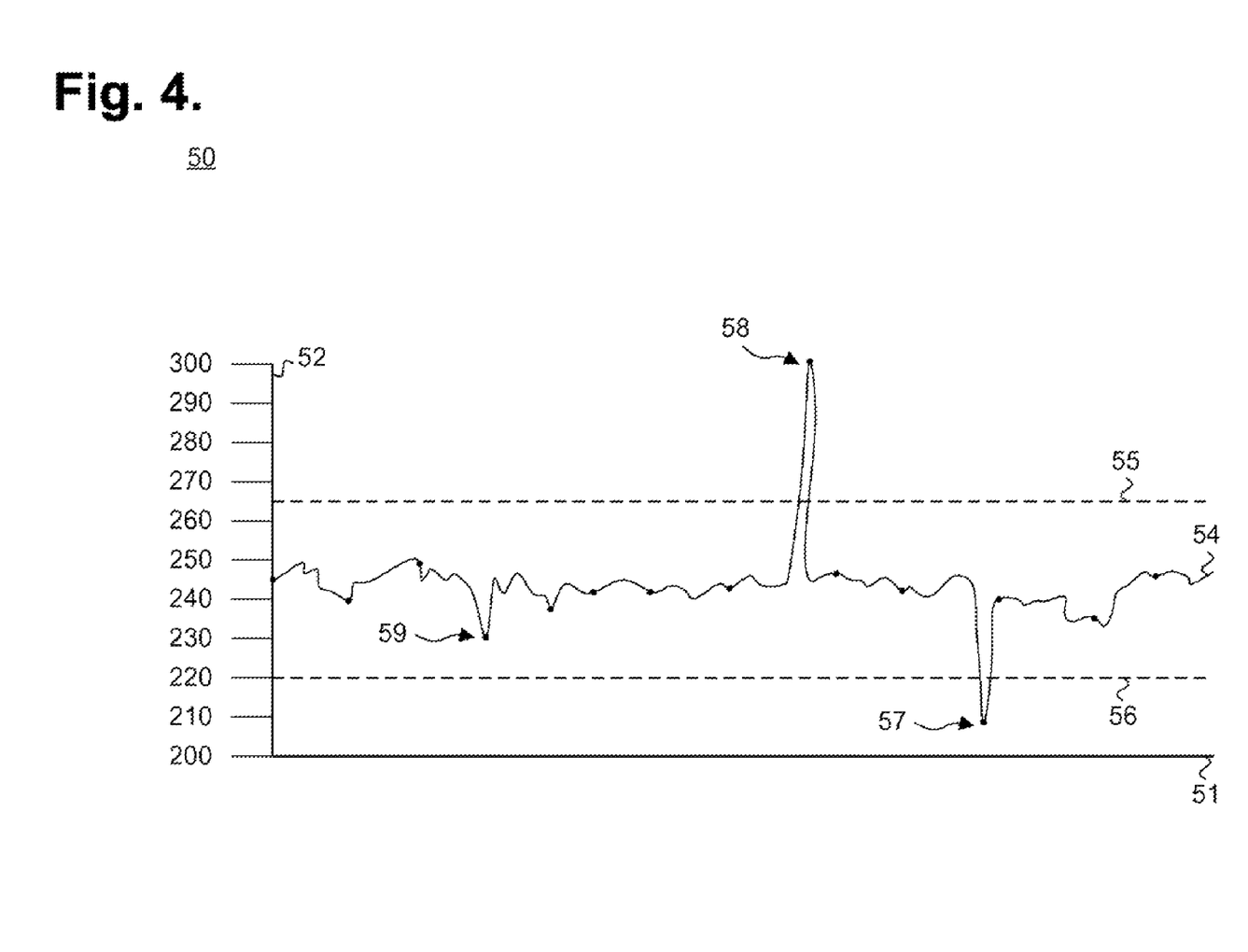
FIG. 4 is a graph showing, by way of example, patient weight versus time points of readings of patient weight.

Alert notifications are configurable to enable triggering of alerts for weight changes of clinical significance, while ignoring changes that do not have clinical significance. FIG. 4 is a graph 50 showing, by way of example, patient 14 weight versus time points of readings of patient weight for use in the method of FIG. 2. The x-axis 51 represents daily weight data readings. The y-axis 52 represents patient weight. The relationship between weight and time is provided as a data line 54. A patient baseline weight is determined, as discussed above with reference to FIG. 3. Upper 55 and lower 56 weight offsets of a prescribed extent are set. The weight offsets 55, 56 can be used individually or in combination.

Patient weight is measured on a regular basis and once a weight datum 57 exceeds the weight offset 56, an alert notification is generated. In a further embodiment, not all data exceeding the weight offset will generate an alert notification. For example, a weight change that lasts for a short duration or is too large may not have clinical significance. A friend or relative of the patient may have stepped on the weight monitoring device 12 leading to an incorrect weight datum 58 and possible alert notification. Likewise, a patient may have a sudden fluid build-up leading to a sudden increase in weight, followed by diuretics, causing the weight to go back down. Again, the patient's physician may not consider the weight gain clinically significant. The alert notification can be configured to require the weight to exceed the weight offset for a period of time, for example, a certain number of days, to generate an alert.

Alert notifications can be generated for each weight datum that exceeds the weight offsets. In a further embodiment, the system is configurable to generate the alert notification only once when a patient's weight exceeds an offset or to repeat the notification for each weight datum outside of the offset. Other forms of alert notifications are possible, such as tiered alert notifications, as further described below with reference to FIG. 10.

In a further embodiment, a short-term weight change 59 within the weight offsets 55, 56 will generate an alert notification. Sudden, short-term weight changes can have clinical significance, but can go undetected if the weight change is within the weight offsets 55, 56. Generating an alert for a specific weight change in a short period of time allows the clinician to respond with appropriate action. The alerts are configurable as discussed above.

Baseline Weight Extrinsic Conditions

Figure 5:
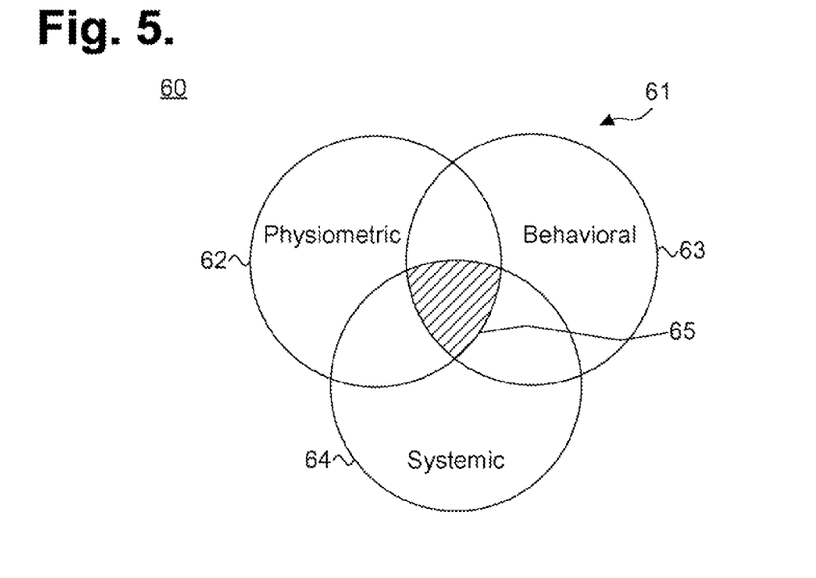
FIG. 5 is a Venn diagram showing, by way or example, baseline weight extrinsic conditions.

A variety of extrinsic conditions, both physical and non-physical, can be factored into the determination of the baseline weight of a patient 14. FIG. 5 is a Venn diagram 60 showing baseline weight extrinsic conditions 61. Extrinsic conditions 61 can affect baseline weight determination, as discussed below with reference to FIGS. 6, 7, and 8. A correction coefficient based on the extrinsic conditions 61 can be used to adjust or correct the weight data used to determine the baseline weight of the patient 14. Each individual weight datum, or any combination thereof, can be adjusted or corrected.

Extrinsic conditions 61 can include physiometric 62, behavioral 63, and systemic 64 conditions. Physiometric conditions 62 include transient, permanent, and cyclic factors, as discussed below with reference to FIG. 6. Behavioral conditions 63 include aspects of patient 14 behavior, as discussed below with reference to FIG. 7. Systemic conditions 64 pertain to the collection of the weight measurement itself, as discussed below with reference to FIG. 8.

Individual baseline weight conditions can occur in combination 61, resulting in a confluence 65 of conditions. For example, a non-compliant patient 14 may ingest excess alcohol against physician directions. To avoid the weight increase from the indiscretion being detected, the patient 14 weighs himself at the gym on a scale that he knows measures a weight lower than the scale he normally uses. The weight increase and bad weight datum cancel out, thereby indicating no weight change. Other types of conditions are possible.

Physiometric Conditions

Figure 6:
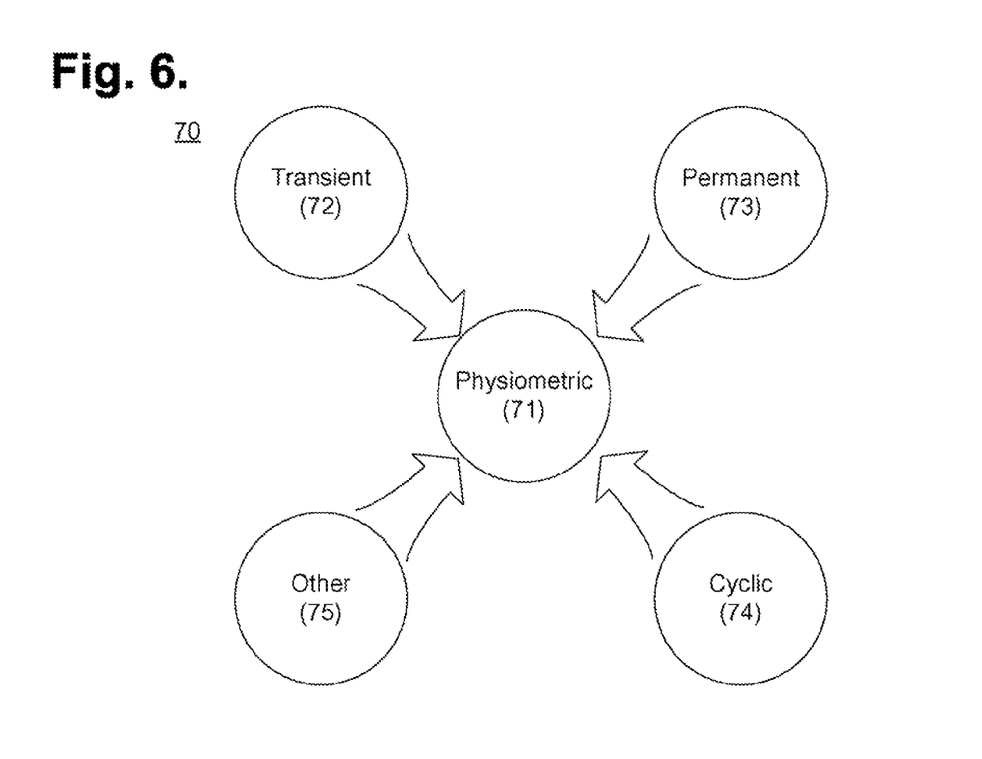
FIG. 6 is a data flow diagram showing, by way of example, types of physiometric conditions.

Physiometric conditions can also be factored into the determination of the baseline weight of a patient 14. Physiometric conditions include changes to the patient's 14 body, whether temporary, permanent, or regularly recurring on a natural basis, which can be identified through remote monitoring. FIG. 6 is a data flow diagram 70 showing, by way of example, types of physiometric conditions 71. Types of physiometric conditions 71 can include transient 72, permanent 73, and cyclic 74 physiometric conditions. Transient 72 physiometric conditions affect the weight of a patient 14 for a short duration and the patient 14 then returns to the previous weight. For example, the intake of salt, alcohol, or medication can cause a short-term change in the weight of a patient 14. Intake of salt, alcohol, or medication can raise the patient's weight, which will return to the pre-intake state after metabolism of the salt or alcohol by the patient.

Permanent 73 physiometric conditions involve a long-term, including permanent, weight change. For example, weight loss or gain by the patient 14 based on changes in diet or exercise regimen, or a stomach stapling procedure can usually lead to long-term weight loss in a patient. Cyclic 74 physiometric conditions occur on a regularly repeated basis. For example, the female menstrual cycle is often accompanied by monthly weight gain and losses due to water retention. Other 75 physiometric conditions are possible.

Using the female menstrual cycle as an example, physiometric conditions can be used to adjust or correct the weight data used to determine the patient's 14 baseline weight. The average menstrual cycle occurs over a twenty-eight day period. A female patient's 14 weight gain from water retention often occurs during the two weeks leading up to her period. The water weight is then lost and the woman's weight returns to normal. Weight data taken during the cycle will vary according to the weight gain and loss. A baseline weight determined using the water weight gain data will not result in a true indication of the patient's 14 baseline weight.

The cyclic weight gain is factored into the weight data as a correction coefficient to determine a baseline weight that is more accurate. For example, patient 14 weight data can be observed on a daily basis. The weight data can be evaluated for the level of influence any water weight gain may have on the weight measurement. Weight data from the weeks that no water weight gain occurs are not adjusted. The data where water weight gain has occurred are adjusted. For example, the correction coefficient can adjust the water weight gain data to compensate for the added water weight by lowering the value of the water weight gain data. In a further embodiment, the water weight gain data can be given a lower weighted value than the other weight data. Other adjustments or corrections are possible. The adjusted or correct weight data can then be used in the determination of the baseline weight.

Behavioral Conditions

Figure 7:
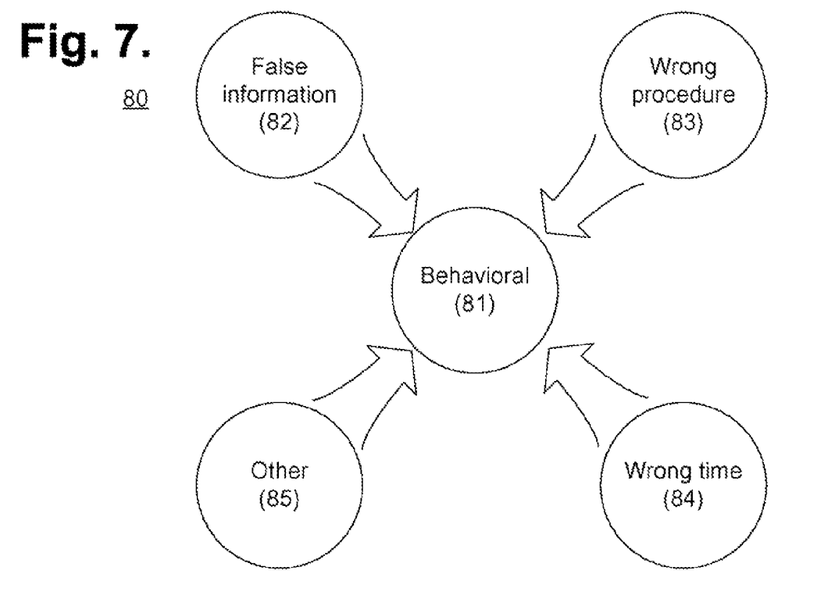
FIG. 7 is a data flow diagram showing, by way of example, types of behavioral conditions.

As well, behavioral conditions can be factored into the determination of the baseline weight of a patient 14. Behavioral conditions included actions undertaken by the patient 14, or a third party, in remotely providing the weight data for baseline determination or during remote monitoring of patient 14 weight. FIG. 7 is a data flow diagram 80 showing, by way of example, types of behavioral conditions 81. Types of behavioral conditions 81 can include false information 82, wrong procedure 83, and wrong time 84 conditions. False information 82 can include conditions where the patient 14 does not provide accurate information. For example, the patient 14 may not be truthful as to his weight by not standing fully on the weight monitoring device 12. Wrong procedure 83 can include the patient 14 incorrectly using the weight monitoring device 12. Wrong time 84 can include the patient 14 weighing himself at times different than prescribed by the procedure. For example, the patient 14 may skip every other day in a weigh-in schedule that requires weight data to be taken every day. Other 85 behavioral conditions are possible.

Any behavioral condition 81 present can be applied to the weight data as a correction coefficient to adjust the weight data used in baseline weight determination. For example, the patient 14 can be inconsistent as to the time that weight data is taken, may miss entire days of a daily weigh-in schedule, or may consistently weigh himself at the correct time from Monday to Friday, but occasionally weigh himself at the incorrect time on Sundays, and completely fail to weigh himself on most Saturdays.

The reliability of the weight data being taken at the correct time and correct day can be factored into the weight data to determine a more reliable baseline weight. The correction coefficient adjusts the weight data to compensate for any irregularity in weigh-in. The weight data from Monday to Friday are not adjusted as they follow the weigh-in schedule. The weight data from the Sunday can be adjusted based how reliably the patient's 14 weigh-in schedule was followed for that day of the week. For example, the weight data from the Monday to Friday weigh-ins can be given a higher weight, or the Sunday weigh-in can be given a lower weight, in a weighted average of the weight data. Likewise, the weight data taken from the Saturday can be adjusted, or if unreliable enough, discarded completely. Other adjustments or corrections are possible. The adjusted or corrected weight data can then be used in the determination of the baseline weight.

Systemic Conditions

Figure 8:
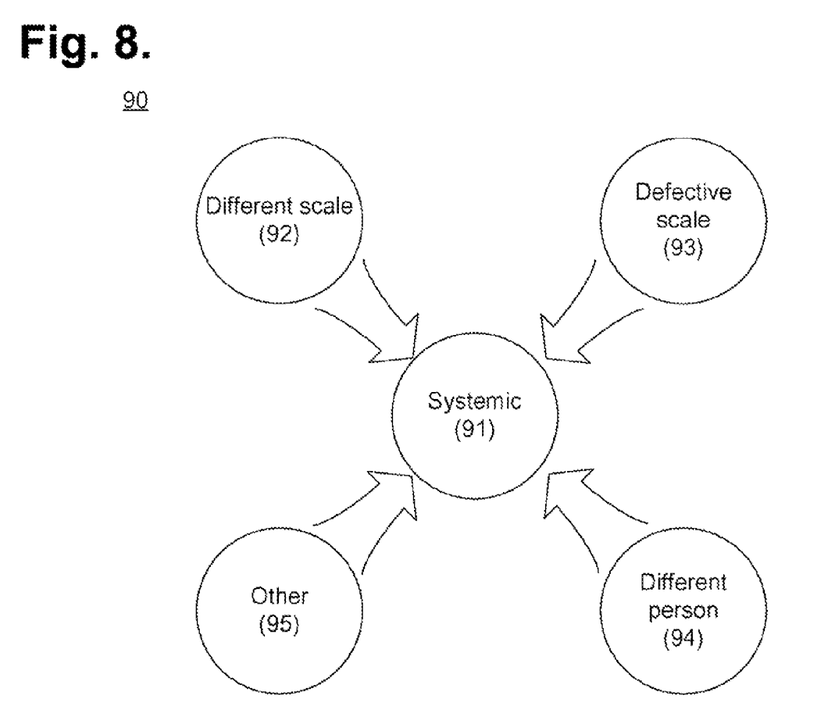
FIG. 8 is a data flow diagram showing, by way of example, types of systemic conditions.

Finally, systemic conditions can be factored into the determination of the baseline weight of a patient 14. Systemic conditions include problems with the weight monitoring device 12, or other device within the automated patient management environment 10, that can result in suspect weight data, whether intentional or not. FIG. 8 is a data flow diagram 90 showing, by way of example, types of systemic conditions 91. Types of systemic conditions 91 can include different scale 92, defective scale 93, and different person 94. Different scales 92 can return different weight data. A patient that takes weight data on different scales can have weight data that vary by a significant amount. Defective scale 94 can include a scale that needs recalibration, has a failing battery, or mechanically measures an incorrect weight for the patient 14. Different person 94 includes someone other than the patient 14 stepping on the scale, which can result in incorrect weight data. Other 95 systemic conditions are possible.

Any systemic condition 91 present can be applied to the weight data as a correction coefficient to adjust the weight data used in baseline weight determination. For example, the accuracy of weight data can be affected by the condition of the weight monitoring device 12, such as a scale. A weight monitoring device 12 that is relatively new or has been recently serviced will normally provide accurate weight data. The weight monitoring device 12 may drift in its readings over time, especially without regular service, and other mechanisms can also cause it to lose its calibration. Additionally, if the patient 14 uses a different weight monitoring device 12 than normal, the accuracy of the different weight monitoring device 12 can be unknown.

The accuracy of the weight monitoring device 12 can be factored into the weight data to determine a more reliable baseline weight. The correction coefficient adjusts the weight data to compensate for any inaccuracy of the weight monitoring device 12. The weight data from the new or newly recalibrated weight monitoring device 12 are not adjusted. The weight data from the out of balance weight monitoring device 12 can be adjusted based on the accuracy of the device 12. For example, the correction coefficient can adjust the weight data to compensate for the out of balance weight monitoring device 12 by lowering or raising the value of the weight data by the amount of inaccuracy in the weight monitoring device 12. In a further embodiment, the weight data from the out of balance weight monitoring device 12 can be given a lower weighted value than the weight data from the calibrated weight monitoring device 12. Likewise, the weight data taken using the different weight monitoring device 12 can be adjusted, or if inaccurate enough, discarded completely. Other adjustments or corrections are possible. The adjusted or corrected weight data can then be used in the determination of the baseline weight.

Actionable Changes

Figure 9:
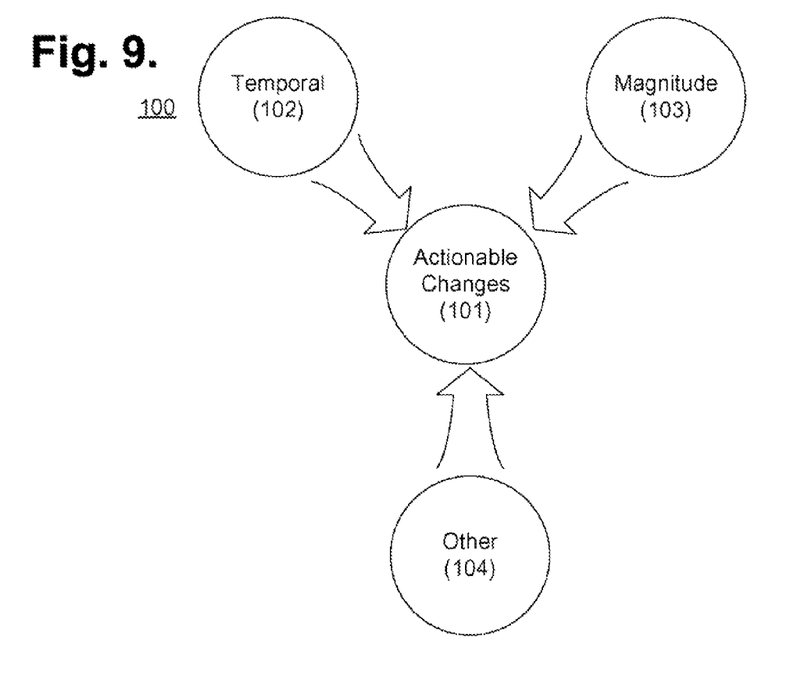
FIG. 9 is a data flow diagram showing, by way of example, types of actionable changes in patient weight.

Certain types of weight change can have clinical significance, in response to which some corrective action may be needed. FIG. 9 is a data flow diagram 100 showing, by way of example, types of actionable changes 101 in patient 14 weight. Types of actionable changes 101 can include temporal 102 and magnitude 103 changes. An example of an action taken based on a change in weight is an alert sent to the patient 14, physician, or hospital, as discussed below with reference to FIG. 10. Temporal 102 changes include weight changes within a period of time. For example, a sudden weight change in a small period of time, such as a day or week, can have clinical significance. Magnitude 103 changes include the amount of change in weight of the patient 14. A large change in weight can signify a trend in health of the patient requiring action by the physician. Other 104 actionable changes in weight are possible.

Tiered Alert Notification

Figure 10:
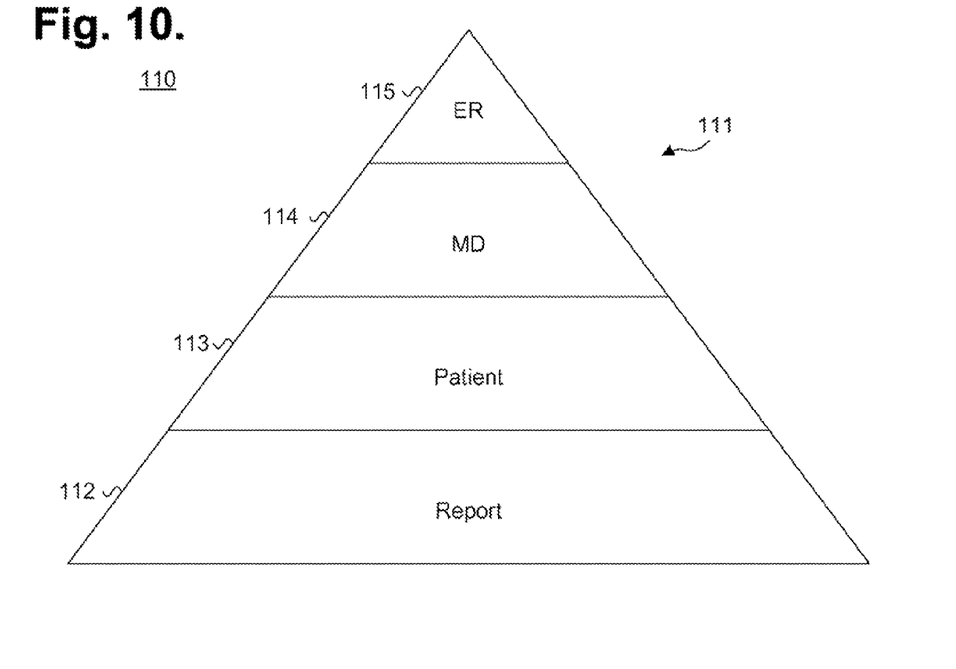
FIG. 10 is a diagram showing tiered alert notification.

Tiered alert notification allows for a progression of alert notifications based on the particular circumstances. Response to an observed weight change can therefore be better adjusted to the circumstances. FIG. 10 is a diagram 110 showing tiered alert notification 111. Tiered alert notification 111 can be provided based on evaluation of the change in patient 14 weight. Four levels of notification can be provided with increasing levels of patient involvement and medical care intervention. At a first level 112, the alert notification is reported but no action is taken in response to the generated alert. At a second level 113, an interpretation of the alert notification, preferably phrased in lay terminology, and related health care information is sent to the patient. At a third level 114, an alert notification is forwarded to the patient's physician or similar health care professionals. Finally, at a fourth level 115, an alert notification is sent to an emergency responder, such as an ambulance. Other alert notifications and levels are possible.

At a basic level, tiered alert notification can be provided by way of a simple interpretation of the collected weight data. The notification could be built up to provide a gradated response to the patient, for example, to notify the patient that he or she is trending into a potential trouble zone. Additionally, human interaction and intervention could be introduced, both by remotely situated and local medical practitioners.

System

Figure 11:
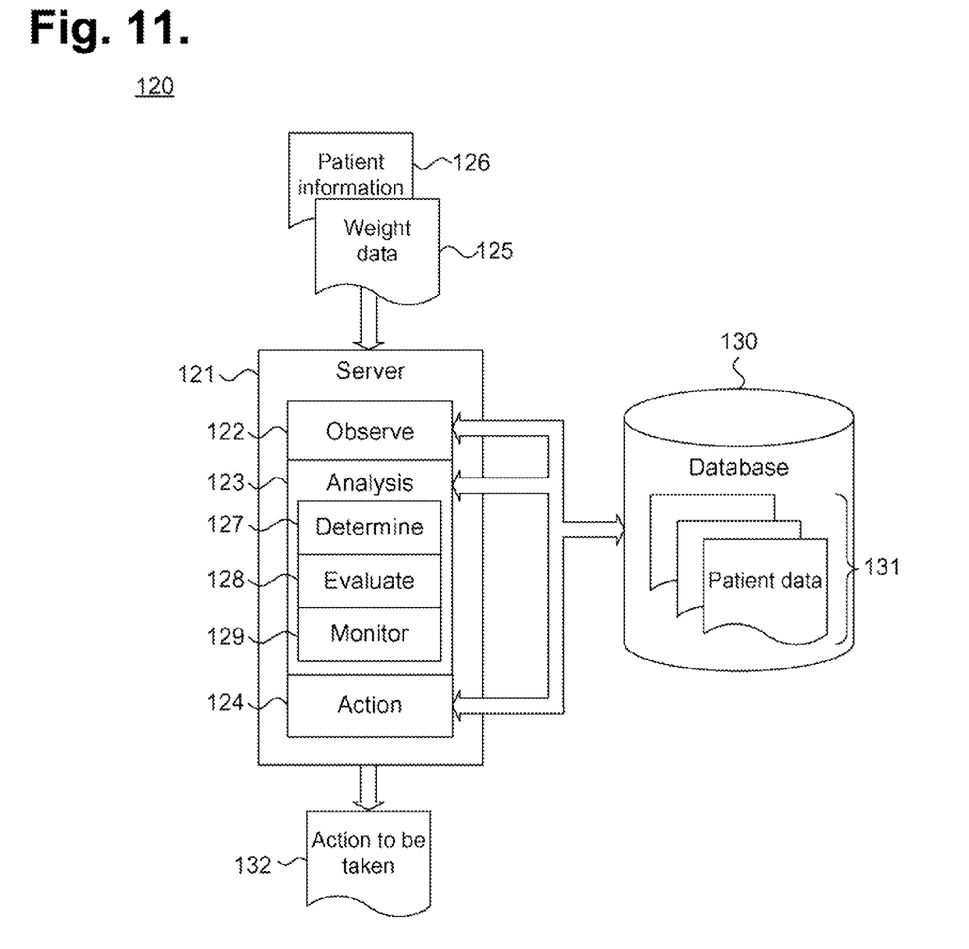
FIG. 11 is a block diagram showing a system for providing enhanced weight alert notification during automated patient management, in accordance with one embodiment.

Generally, the centralized server 13 is responsible for processing of alert notifications for a patient, although, in a further embodiment, the processing can be delegated, for instance, to individual clients 21 or patient management devices 15. FIG. 11 is a block diagram showing a system 120 for providing enhanced weight alert notification during automated patient management, in accordance with one embodiment. The system 120 uses patient weight data remotely received from a weight monitoring device 12 (shown in FIG. 1).

The server 121 includes modules to observe 122, analyze 123, and take action 124. The server 121 is coupled to a database 130 or other form of structured store, within which weight data 125, and other patient information 126, is maintained as patient data 131. Other modules are possible.

The observe module 122 regularly obtains weight data 125 over an observation period from weight monitoring devices 12, and other sources, such as a patient management device 15, which is saved as patient data 131 into a corresponding patient record in the database 130. Other patient information 126 is similarly obtained and stored. The weight data 125 can be requested, or "pulled," from each data source, or unilaterally sent, or "pushed." Other weight monitoring arrangements are possible.

The analysis module 123 includes a determination submodule 127 for determining a baseline weight of the patient 14, as described above with reference to FIG. 2. The analysis module 123 also includes an evaluate submodule 128 for evaluating extrinsic conditions involved with baseline weight determination and adjusting the weight data used to determine the baseline weight accordingly, as described above with reference to FIG. 2. Additionally, the analysis module 123 includes a monitor submodule 129 to monitor the weight of the patient 14 and detect weight changes outside of a prescribed degree, as described above with reference to FIG. 2. Other analysis functions are possible.

Finally, the action module 124 chooses an action to be taken 132 if the patient's weight change cannot be otherwise explained, or as required. The action need not be specifically performed by the server 121, and could instead be dispatched as instructions to a remote system or device, such as a weight monitoring device 12, patient management device, 15, or other device. The action can include providing alert notification 132, as discussed above with reference to FIG. 10. Other actions are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for performing actions in response to enhanced weight monitoring during automated patient management, comprising:
    a baseline weight observation module configured to obtain a plurality of weight measurements remotely measured in an automated patient environment for a patient during an observation period;
    an analysis module configured to determine a raw baseline weight for the patient based on the weight measurements and adjusting the raw baseline weight through processing of irregularities in the weight measurements into a baseline weight;
    a weight observation module configured to obtain weight remotely measured in the automated patient environment for the patient on a substantially regular basis;
    a monitor module configured to identify changes in the weight by periodic comparison to the baseline weight; and
    an action module configured to take action in response to the periodic comparison upon at least one of the changes exceeding a prescribed extent of change over the baseline weight.

2. A system according to claim 1, further comprising:
    a behavioral evaluation module configured to identify behavioral conditions comprising actions undertaken by the patient or a third party affecting how the weight measurements are remotely measured.

3. A system according to claim 2, wherein the behavioral conditions are selected from a group comprising false information provided by the patient or the third party, wrong procedure followed in how the weight measurements are remotely measured, and wrong time of when the weight measurements are remotely measured.

4. A system according to claim 2, further comprising:
    a systemic evaluation module configured to identify systemic conditions comprising data values measured under procedural deviation from how the weight measurements are remotely measured; wherein the systemic conditions are selected from a group comprising different scale used in remotely measuring the weight, defective scale used in remotely measuring the weight, and a person other than the patient weighed for the weight.

5. A system according to claim 1, wherein the baseline weight is a result of a cumulative analysis based on one of the plurality of weight measurements of the observation period or a subset of the plurality of weight measurements of the observation period.

6. A system according to claim 1, wherein the baseline weight is a result of a statistical analysis expressed as:

$$w_{BL} = f(w_i; \{w_1, w_2, w_3, \ldots, w_n\})$$

where $w_{BL}$ is baseline weight, $f(w_i)$ is a statistical function that includes the adjustment of the irregularities, and n is number of individual weight measurements from the observation period.

7. A system according to claim 1, wherein the action comprises an alert notification adjusted to fit the changes in patient weight.

8. A system according to claim 1, wherein the raw baseline weight is determined from a range of weight measurements comprising a first period of weight measurements, a last period of weight measurements, a next period of weight measurements, and a floating period of weight measurements.

9. A method for performing actions in response to enhanced weight monitoring during automated patient management, comprising:
    obtaining a plurality of weight measurements remotely measured in an automated patient environment for a patient during an observation period;
    determining a raw baseline weight for the patient based on the weight measurements and adjusting the raw baseline weight through processing of irregularities in the weight measurements into a baseline weight;
    obtaining weight remotely measured in the automated patient environment for the patient on a substantially regular basis;
    identifying changes in the weight by periodic comparison to the baseline weight; and
    taking action in response to the periodic comparison upon at least one of the changes exceeding a prescribed extent of change over the baseline weight, wherein the baseline weight is a result of a statistical analysis expressed as:

$$w_{BL} = f(w_i; \{w_1, w_2, w_3, \ldots, w_n\})$$

where $w_{BL}$ is baseline weight, $f(w_i)$ is a statistical function that includes the adjustment of the irregularities, and n is number of individual weight measurements from the observation period.

10. A method according to claim 9, further comprising:
identifying behavioral conditions comprising actions undertaken by the patient or a third party affecting how the weight measurements are remotely measured.

11. A method according to claim 10, wherein the behavioral conditions are selected from a group comprising false information provided by the patient or the third party, wrong procedure followed in how the weight measurements are remotely measured, and wrong time of when the weight measurements are remotely measured.

12. A method according to claim 9, further comprising:
identifying systemic conditions comprising data values measured under procedural deviation from how the weight measurements are remotely measured, wherein the systemic conditions are selected from a group comprising different scale used in remotely measuring the weight, defective scale used in remotely measuring the weight, and a person other than the patient weighed for the weight.

13. A method according to claim 9, wherein the baseline weight is a result of a cumulative analysis based on one of the plurality of weight measurements of the observation period or a subset of the plurality of weight measurements of the observation period.

14. A method according to claim 9, wherein the action comprises an alert notification adjusted to fit the changes in patient weight.

15. A method according to claim 9, wherein the raw baseline weight is determined from a range of weight measurements comprising a first period of weight measurements, a last period of weight measurements, a next period of weight measurements, and a floating period of weight measurements.

16. A system for providing enhanced weight alert notification during automated patient management, comprising:
a baseline weight observation module configured to obtain a plurality of weight measurements remotely in an automated patient environment from a weight monitoring device for a patient during an observation period;
a determination module configured to determine a raw baseline weight for the patient based on a function of the weight measurements;
an analysis module configured to identify irregularities in the weight measurements;
an evaluation module configured to adjust the raw baseline weight through processing of the irregularities into a baseline weight;
a weight observation module configured to obtain weight remotely measured in the automated patient environment for the patient on a substantially regular basis;
a monitor module configured to identify changes in the weight by periodic comparison to the baseline weight; and
an alert module configured to generate an alert notification in response to the change in weight.

17. A system according to claim 16, wherein the alert notification adjusted to fit the changes in patient weight.

18. A system according to claim 16, further comprising:
an error module configured to check the weight measurements against an error range and to discard the weight measurements outside the error range from the raw baseline weight.

19. A system according to claim 16, wherein the determination module is further configured to redetermine the raw baseline weight for the patient based on the function of the weight measurements from a further observation period.

20. A method for providing enhanced weight alert notification during automated patient management, comprising:
obtaining a plurality of weight measurements remotely in an automated patient environment from a weight monitoring device for a patient during an observation period;
determining a raw baseline weight for the patient based on a function of the weight measurements;
identifying irregularities in the weight measurements;
adjusting the raw baseline weight through processing of the irregularities into a baseline weight;
obtaining weight remotely measured in the automated patient environment for the patient on a substantially regular basis;
identifying changes in the weight by periodic comparison to the baseline weight; and
generating an alert notification in response to the change in weight.

21. A method according to claim 20, wherein the alert notification adjusted to fit the changes in patient weight.

22. A method according to claim 20, further comprising:
checking the weight measurements against an error range; and
discarding the weight measurements outside the error range from the raw baseline weight.

23. A method according to claim 20, further comprising:
redetermining the raw baseline weight for the patient based on the function of the weight measurements from a further observation period.

* * * * *